United States Patent [19]

McKinley

[11] Patent Number: 5,191,203
[45] Date of Patent: Mar. 2, 1993

[54] STEREO VIDEO ENDOSCOPE OBJECTIVE LENS SYSTEM

[75] Inventor: Harry P. McKinley, Southampton, Mass.

[73] Assignee: McKinley Optics, Inc., Southampton, Mass.

[21] Appl. No.: 868,706

[22] Filed: Apr. 15, 1992

Related U.S. Application Data

[63] Continuation-in-part of Ser. No. 687,330, Apr. 18, 1991, Pat. No. 5,122,650.

[51] Int. Cl.$^5$ .............................................. H01J 40/14
[52] U.S. Cl. .................... 250/208.1; 359/480; 359/652
[58] Field of Search ................... 250/208.1, 558; 128/4–7; 358/98; 359/377, 641, 652–654, 480, 481

[56] References Cited

U.S. PATENT DOCUMENTS

| | | | |
|---|---|---|---|
| 3,655,259 | 4/1972 | Miyauchi et al. | 359/376 |
| 4,061,135 | 12/1977 | Widran et al. | 359/401 |
| 4,217,025 | 8/1980 | Takenaka | 359/480 |
| 4,448,495 | 5/1984 | Muller et al. | 359/377 |
| 4,518,231 | 5/1985 | Muchel et al. | 359/377 |
| 4,615,332 | 10/1986 | Buess et al. | 128/6 |
| 4,651,201 | 3/1987 | Schoolman | 128/6 |
| 4,787,734 | 11/1988 | Matsumura | 359/377 |
| 4,824,228 | 4/1989 | Wickholm et al. | 359/462 |
| 4,862,873 | 9/1989 | Yajima et al. | 359/462 |
| 4,873,572 | 10/1989 | Miyazaki et al. | 128/6 |
| 4,895,431 | 1/1990 | Tsujuchi et al. | 359/107 |
| 4,926,257 | 5/1990 | Miyazaki | 128/6 |
| 5,122,650 | 6/1992 | McKinley | 250/208.1 |

FOREIGN PATENT DOCUMENTS 0211783 7/1986 European Pat. Off. .

Primary Examiner—David C. Nelms
Assistant Examiner—Stephone B. Allen
Attorney, Agent, or Firm—Lahive & Cockfield

[57] ABSTRACT

A stereoscopic objective lens system for video endoscopes and borescopes includes a full diameter collimator lens systems and a pair of half-diameter stereo lens systems. The lens systems can be formed of doublet lenses or a combination of singlet and doublet lenses, or of gradient index lenses, or of a mixture of such lenses. The full-diameter lens system collimates object points, imaging object points to infinity to present equal-angle pairs from symmetrically disposed object points to the small stereo pair. This equal-angle property enables accurate object/image mapping onto the final stereo image pair, such that all parts of each left/right image can be mapped to within a fraction of a video pixel to each other.

17 Claims, 7 Drawing Sheets

STEREO VIDEO ENDOSCOPE OBJECTIVE LENS SYSTEM

BACKGROUND OF THE INVENTION

This application is a Continuation-In-Part of U.S. patent application Ser. No. 687,330 filed Apr. 18, 1991, now U.S. Pat. No. 5,122,650.

This invention relates generally to optical lens systems, and, more particularly, relates to stereoscopic objective lens designs adapted for use in stereo video endoscopes.

Medical endoscopes are widely utilized to view internal regions of the human body during diagnostic, surgical, and other medical procedures. Endoscopes typically include a long, thin, rigid or semi-rigid optical cylinder affixed to a viewing mechanism. The cylinder is sufficiently narrow to be inserted through a small opening in the body, which may be natural or surgical. When the endoscope is inserted and positioned for use, an image of the object being viewed is formed at an inserted end of the endoscope by an objective lens. The image passes through a series of relay lenses down the cylinder to an eye lens or video camera at a viewing end of the endoscope.

In recent years, researchers have attempted to improve the imaging available through endoscopic devices by developing stereoscopic video endoscopes. These endoscopes present an apparently three-dimensional image on a video monitor. The stereoscopic effect is created by producing two optical images—a left image and a right image—through the endoscope. The left and right optical images are presented by the endoscope to left and right image sensors, which may be charge-coupled device (CCD) cameras or other image sensing devices. The sensing devices convert the left and right optical images into left and right video images which are then presented as alternating left-right images on a monitor, at a switching rate higher than the flicker-sensing limit of the human eye, so that observed images appear flicker-free.

The images are alternately switched from a left-hand polarization mode to a right-hand polarization mode, such that, for example, the left image has a left-hand polarization and the right image has a right-hand polarization. In accord with his example, the observer wears polarized glasses in which the left lens has the left-hand polarization and the right lens has the right-hand polarization. Thus, the left eye sees only images from the left channel of the endoscope system and the right eye sees only images from the right channel, resulting in stereoscopic viewing.

The following U.S. and foreign patents disclose examples of stereo endoscopes, some of which utilize video imaging and display elements:

| U.S. | 4,061,135 |
| U.S. | 4,615,332 |
| U.S. | 4,651,201 |
| U.S. | 4,862,873 |
| U.S. | 4,873,572 |
| U.S. | 4,895,431 |
| EP | 211,783 |

In particular, U.S. Pat. No. 4,061,135 discloses a binocular endoscope in which images are transmitted from the viewed object to the viewing station through an optical system utilizing a dove prism and mechanical linkage to compensate for rotation effects.

U.S. Pat. No. 4,615,332 discloses a binocular endoscope having flexible light guides and binocular eyepieces.

U.S. Pat. No. 4,651,201 discloses a stereoscopic video endoscope including two image guides and an illumination light guide. The image guides are optically coupled to a stereoscopic viewer for three dimensional viewing. The viewer includes couplings for attaching miniature video cameras that can be connected to a head-mounted stereoscopic video display.

U.S. Pat. No. 4,862,873 discloses a stereo endoscope having two light guides for carrying images of an object to an electro-optical imaging assembly. A lens system directs light from the object to the objective end of the light guides. Illuminating light is transmitted to the object from the opposite end of one light guide, thereby illuminating the object. Simultaneously, the image transmitted through the other optical guide is conducted to the imaging assembly.

U.S. Pat. No. 4,873,572 discloses a stereo endoscope having a CCD camera module and two image-forming lens systems that form two object images. The object images are integrated and directed to the CCD camera to provide a stereoscopic output. The lens systems include red, green, and blue color filters disposed at the camera imaging surface.

U.S. Pat. No. 4,895,431 discloses an endoscope apparatus that generates a three-dimensional image of an object from overlapping images recorded by a camera. The endoscope includes an insertion module and a movable end section capable of being deflected through an angle. A first image is recorded with the end section positioned at a first angle. A second image, partially overlapping the first image, is recorded after moving the end section to a second angle. The relative position of the movable end section is detected by an encoder that generates position signals for input to a microprocessor, which utilizes the position signals to generate a three-dimensional image of the object.

European Patent No. 211,783 discloses a stereo video endoscope in which two light pipes deliver two images of the same object. These images are presented by a binocular device to the user's eyes to show a three dimensional image of the target. The apparatus includes two television cameras and video recorders for recording the images. The recorded images can be displayed on separate screens and viewed by a binocular viewing system.

Most conventional stereo endoscopes, however, share a number of deficiencies associated with their objective lens systems. These problems include a bulky and unwieldy configuration; high cost and complexity of fabricating the objective lens system; and the mediocre optical performance afforded by conventional objective lens systems.

An additional problem associated with conventional stereo video endoscope objectives involves the requirement that all portions of each left/right image be mapped to within a fraction of a video pixel to each other. This pixel mapping condition is a significant optical design constraint, because the object-to-image ray paths through the lens system are quite different for the left and right image points associated with a common object point.

Accordingly, it is a general object of the present invention to provide improved stereo endoscope objective lens systems that overcome the problems associated with conventional designs.

A more specific object is to provide an improved stereo endoscope objective lens system having optical elements that facilitate assembly of the system.

It is another object of the invention to provide an improved stereo endoscope objective lens system having elements that are substantially less expensive to manufacture than the elements of conventional systems.

A further object is to provide an improved stereo endoscope objective lens system having optical performance characteristics that are substantially superior to the performance characteristics of conventional systems.

Another object of the invention is to provide a stereo objective lens system affording a pixel mapped image.

The above and other objects and advantages of this invention will become more readily apparent when the following description is read in conjunction with the accompanying drawings.

SUMMARY OF THE INVENTION

The foregoing objects are attained by the invention, which provides an improved stereo endoscope objective lens system for video imaging in medical endoscopes and industrial borescopes.

One aspect of the invention includes two full-diameter doublets and a double set of two half-diameter identical doublets. The full-diameter doublets substantially collimate object points, i.e., image them substantially to infinity.

In accord with this aspect of the invention, most of the optical power necessary to accomplish this collimation is provided by in the first or outer doublet, while the second collimator doublet is of low power.

In a further aspect of the invention, the smaller doublets are identical, so that they can be most economically fabricated in production quantities. This is advantageous because these small lenses are inherently difficult to manufacture.

In another aspect of the invention, the large collimator lens system presents equal-angle pairs from symmetrically disposed object points to the small stereo lens systems. This equal-angle solution provides accurate object/image mapping onto the final stereo image pair. In this design, the larger, and hence easier to fabricate, collimator lens system carries the corrective burden, so that the smaller, more difficult to manufacture lenses can be made as simple as possible.

In still another aspect of the invention the collimator lens system may be formed of a combination of singlet and doublet lenses.

In another embodiment gradient index (GRIN) lenses can be substituted for either the collimator doublets or the stereo doublet pairs or both. These lenses are more economical to fabricate and can be constructed to produce the same ray bending and hence the same optical output as the doublet lenses.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and the accompanying drawings, in which.

DESCRIPTION OF ILLUSTRATED EMBODIMENTS

Figure 1:
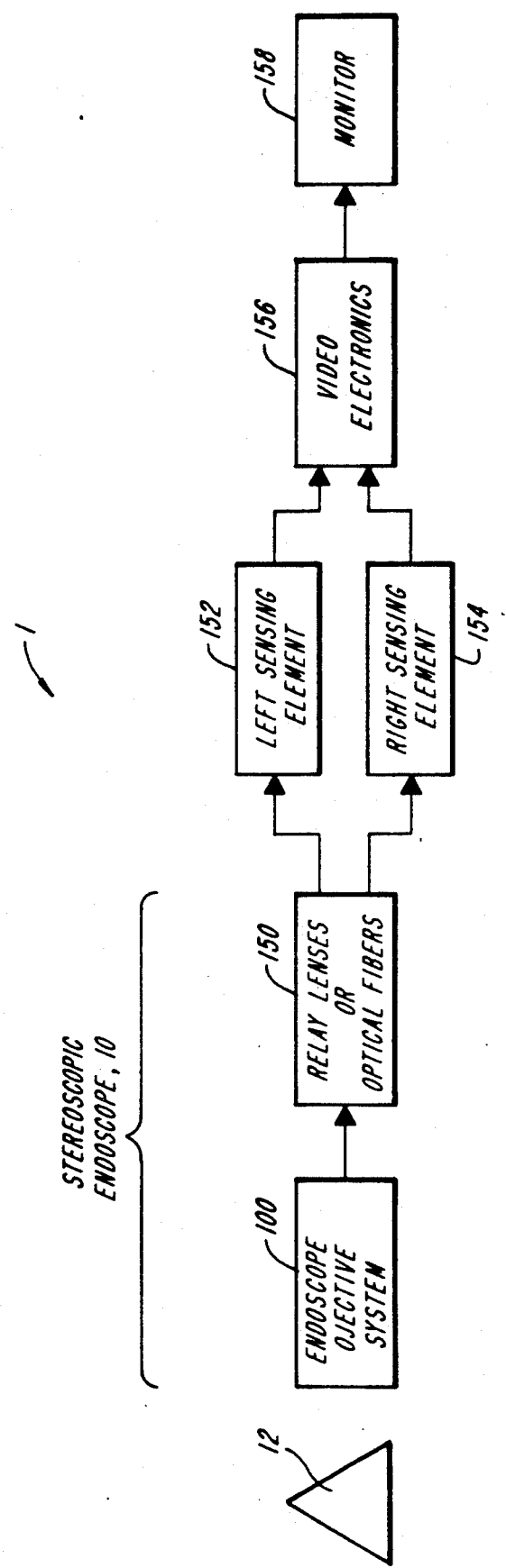
FIG. 1 is a schematic diagram depicting a stereo video endoscope utilizing an objective lens system constructed in accordance with the invention.

FIG. 1 depicts the invention, an endoscope objective system 100, utilized in a stereo video endoscopy system 1 for generating stereoscopic images of an object 12. The system 1 includes a stereoscopic endoscope 10 containing objective system 100; sensing modules 152, 154; switching module 156; and a monitor 158. In addition to objective lens system 100, the endoscope 10 includes conventional relay lenses or optical fibers 150 for transmitting light collected by the endoscope objective system 100 to light sensing modules 152, 154.

The endoscope objective system 100 generates left and right optical images of the object 12 that are processed by sensing elements 152, 154 and video switching module 156 in a known manner to display an apparently three-dimensional image of the object 12 on video monitor 158.

The stereoscopic effect is created by producing two optical images—a left image and a right image—through the endoscope objective system 100. The left and right optical images generated by the objective system 100 are presented by the relay lens or optical fiber system 150 to left and right image sensors 152, 154, which can be conventional charge-coupled device (CCD) cameras or other image sensing devices. The CCD elements operate in a known manner to convert the light collected by the objective system 100, and transmitted by the relay lenses or optical fibers 150, into electrical signals representative of the left and right optical images of the object 12.

Conventional video switching circuitry 156 transmits the electronic signals representative of left and right video images as alternating left-right images on the monitor 158. In accord with known video practice, these alternating images are presented at a switching rate higher than the flicker-sensing limit of the human eye, so that observed images appear flicker-free.

Moreover, the images can be alternately switched from a left-hand polarization mode to a right-hand polarization mode, such that, for example, the left image has a left-hand polarization and the right image has a right-hand polarization. The observer wears polarized glasses in which the left lens has the left-hand polarization and the right lens has the right-hand polarization.

Thus, when the observer views the monitor 158, the left eye sees only images from the left channel of the endoscope system and the right eye sees only images from the right channel, resulting in stereoscopic viewing. Video switching and display equipment of this type is commercially available from Stereographics, Inc. of San Rafael, Calif.; and from Tektronix Corp., of Beaverton, Oreg.

Figure 2:
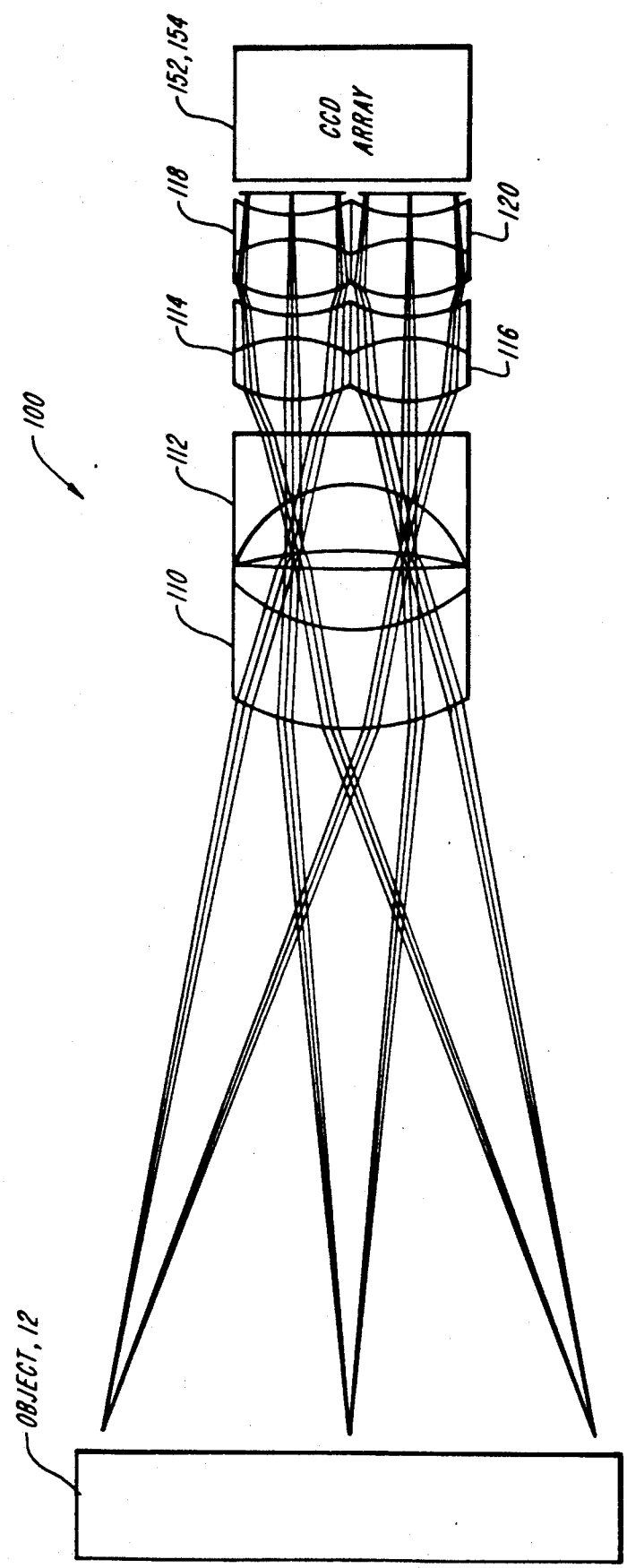
FIG. 2 is an optical schematic diagram depicting an objective lens system constructed in accordance with the invention, showing light rays transmitted through the system.
Figure 3:
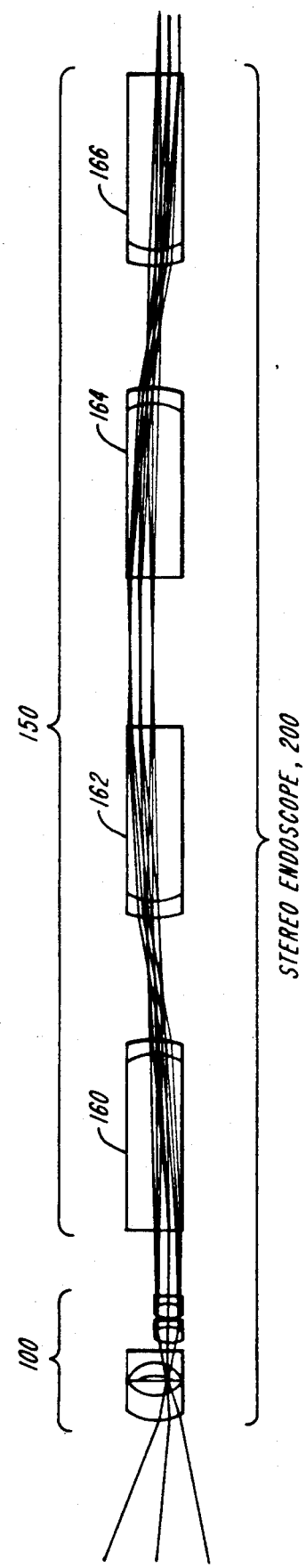
FIG. 3 is an optical schematic diagram depicting the objective lens system of FIG. 2 in combination with relay lenses for transmitting the optical images.

The accuracy and quality of the image displayed on monitor 158 is controlled by the performance of the endoscope objective system 100, which is the subject of the present invention. FIGS. 2 and 3 depict an objective lens system 100 constructed in accordance with the invention, showing light rays transmitted through the system. FIGS. 2 and 3 depict the same system, with two elements being omitted from FIG. 3 for purposes of clarity.

As indicated in FIG. 2, one embodiment of the objective system 100 includes two full-diameter doublets 110, 112 and a double set of two half-diameter identical doublets 114, 116, 118, 120. The full-diameter doublets collimate object points, i.e., image them to infinity. In accordance with the invention, most of the optical power required to accomplish this collimation is provided by the first collimator doublet 110 closest to the object 12, while the second collimator doublet 112 can have a very low optical power.

Those skilled in the art will appreciate that the lenses of the objective system 100 depicted in FIG. 2 define a sequence of sixteen optical surfaces. A working example of a set of lenses for objective system 100 is set forth below in Table A.

TABLE A

| SURFACE | RADIUS | THICKNESS | APERTURE | GLASS |
|---|---|---|---|---|
| 1 | — | −4.002608 | 0.225000 | AIR |
| 2 | 6.211875 | 2.500000 | 3.000000 | SK5 |
| 3 | 4.462623 | 1.500000 | 3.000000 | SF8 |
| 4 | 53.596342 | 0.400000 | 3.000000 | AIR |
| 5 | −11.075366 | 1.600000 | 2.500000 | SK5 |
| 6 | −3.318618 | 1.500000 | 3.000000 | SF8 |
| 7 | −31.896589 | −1.200000 | 2.500000 | AIR |
| 8 | — | 1.900000 | 0.464074 | AIR |
| 9 | 2.747539 | 1.600000 | 1.500000 | SSKN8 |
| 10 | −3.153676 | 0.700000 | 1.500000 | SF1 |
| 11 | 4.815753 | 0.250000 | 1.500000 | AIR |
| 12 | 2.747539 | 1.600000 | 1.500000 | SF1 |
| 13 | −3.153676 | 0.700000 | 1.500000 | SSKN8 |
| 14 | 4.815753 | 0.400000 | 1.500000 | AIR |
| 15 | — | 0.001000 | 1.400000 | BK7 |
| 16 | — | — | 1.400000 | AIR |

In Table A, the numerical value in the "RADIUS" and "THICKNESS" columns are set forth in millimeters. The "GLASS" descriptions are standard optical glass characterizations as found in the product catalog of the Schott Glass Company of the Federal Republic of Germany. The "THICKNESS" column refers to the distance to the next optical surface. For example, in connection with surface 3, the number 1.5000 signifies 1.5 millimeters to surface 4. The column "RADIUS" refers to the radii of curvature of the respective curved surfaces. In this working example, the lens diameters are 6 millimeters for the large doublets and 3 millimeters for the small doublets. The 14 overall object-to-image distance is 28.3 millimeters. The image diameter is 2.5 millimeters.

Figure 4:
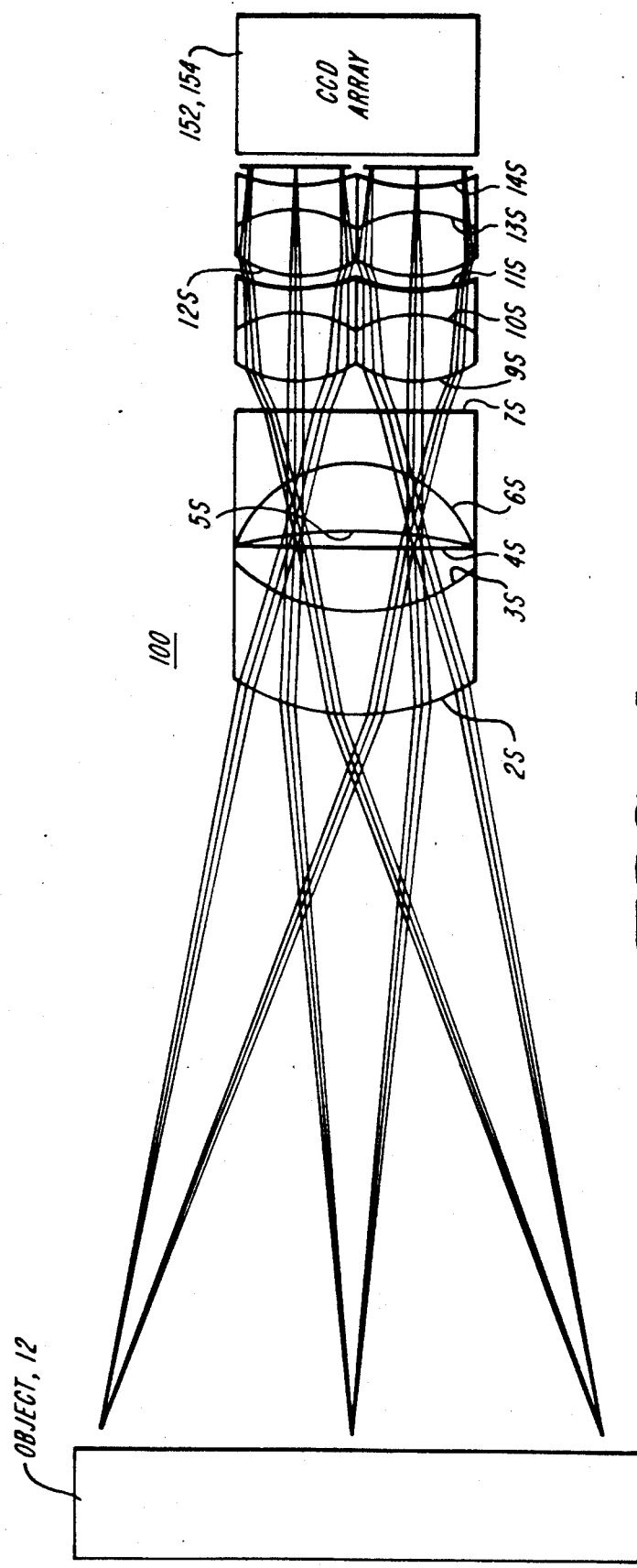
FIG. 4 is an optical schematic diagram of the objective lens system of FIG. 2 illustrating the location of the surfaces specified in Table A.

In Table A, the surfaces correspond to the labeled surfaces in FIG. 4. The surfaces in the table identified as 1, 8, 15 and 16 do not correspond to actual surfaces, but are artifacts introduced by the specific program employed to generate this table. For clarity the numbered surfaces from table A are designated with an S following the numeral, for example, the surface designated 2S in FIG. 4 corresponds to the surface 2 in table A.

The system 100 is designed so that all parts of each left/right image are mapped to within a selected distance of each other such that stereoscopic image quality is maintained. For video applications, this selected distance is typically a fraction of a video pixel. This is a difficult condition to satisfy, because the object-to-image ray paths through the lens system are quite different for the left and right image points of a common object point. FIG. 2 clearly illustrates this path difference. The ray paths shown in FIG. 2 demonstrate how differently an object point is imaged through the lens elements for the left and right images.

The objective system 100 depicted in FIG. 2 is able to map all parts of each left/right image to within a fraction of a video pixel to each other, because the large collimator doublets present equal-angle pairs from symmetrically disposed object points to the small stereo doublet pairs.

This exact equal-angle solution results in an accurate object/image mapping onto the final stereo image pair. Accuracy is also enhanced by the combination of a first high power collimator doublet 110 and a second, lower power collimator doublet 112. This second doublet 112 strongly influences the optical solution to the image-mapping problem.

A further advantage is provided in that the smaller doublets 114, 116, 118, and 120 are identical, so that they can be most economically fabricated in production quantities. This characteristic tends to offset the inherent difficulty of manufacturing small lenses. The larger, and hence easier to fabricate, doublets carry the corrective burden, so that the smaller, more difficult to manufacture lenses can be as simple as possible.

Figure 5:
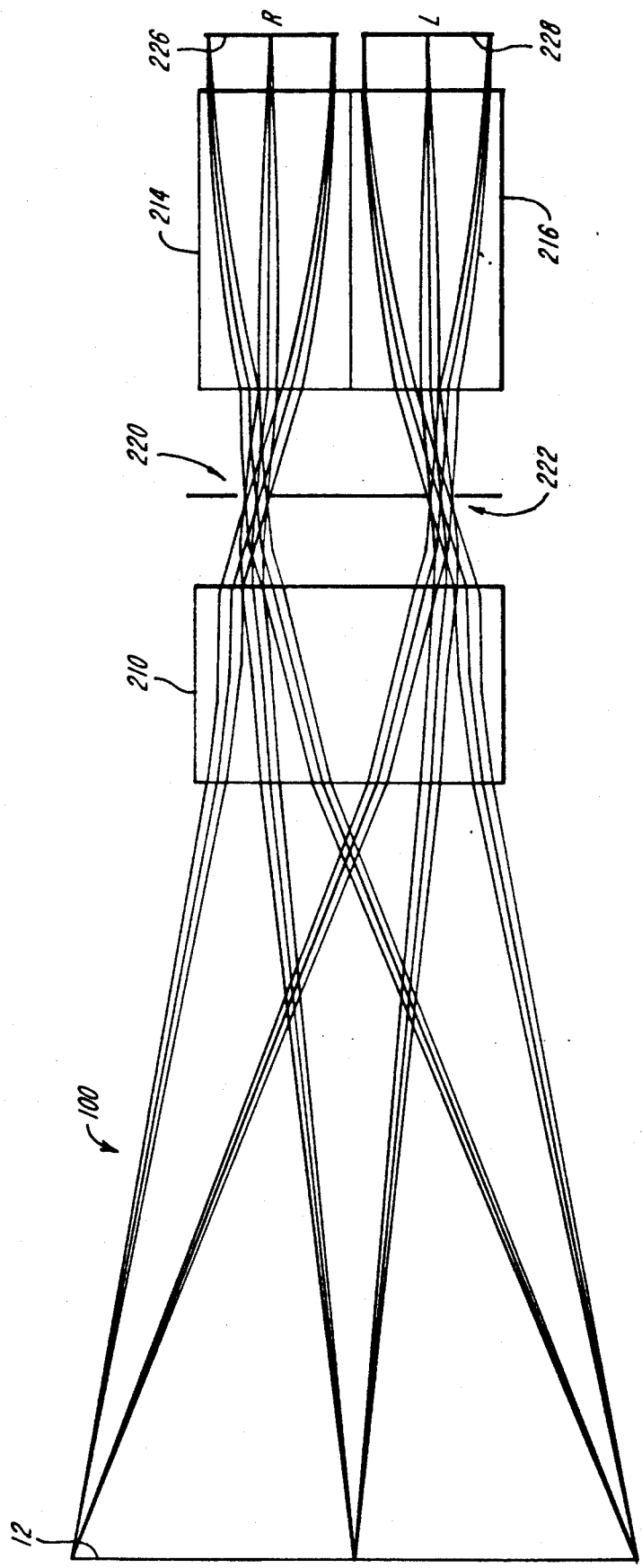
FIG. 5 is a optical diagram of the objective lens system of FIG. 2 incorporating gradient index lenses in place of the doublet lenses.

FIG. 5 illustrates an objective system 100 where the lens systems are formed of gradient index lenses (GRINS) in place of the doublet lenses. These lenses can be manufactured to duplicate the optical performance of the doublet lenses. In FIG. 5 a full diameter GRIN collimator lens 210 performs the collimator function and a matched pair of GRIN one half diameter stereo lenses 214 an 216 complete the objective lens assembly. The pair of stereo lenses produce left and right images 226 and 228 on the image plane. (A pair of aperture stops 220 and 222 may be employed to define the pupils.)

Of course aperture stops may be placed at other locations in the objective lens system according to the purposes of the designer.

Figure 6:
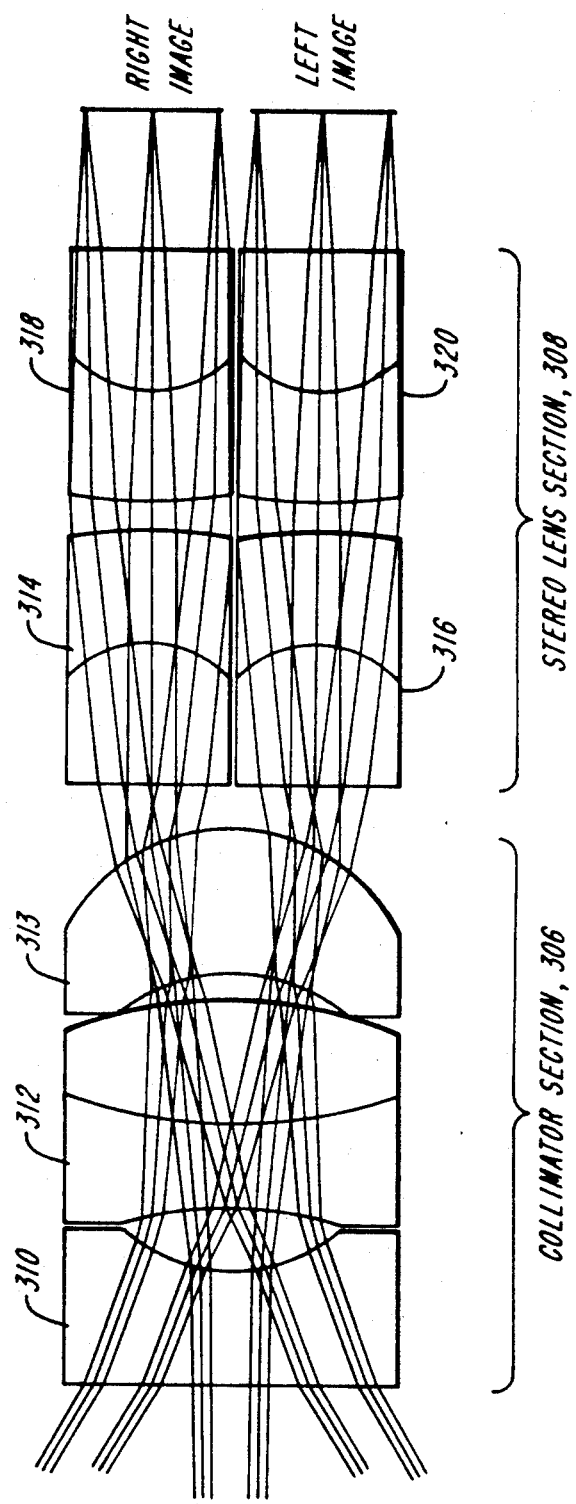
FIG. 6 and 7 are optical schematic diagrams depicting an objective lens system constructed in accordance with the invention wherein the collimating lens system is formed of a combination of singlet and doublet lenses.
Figure 7:
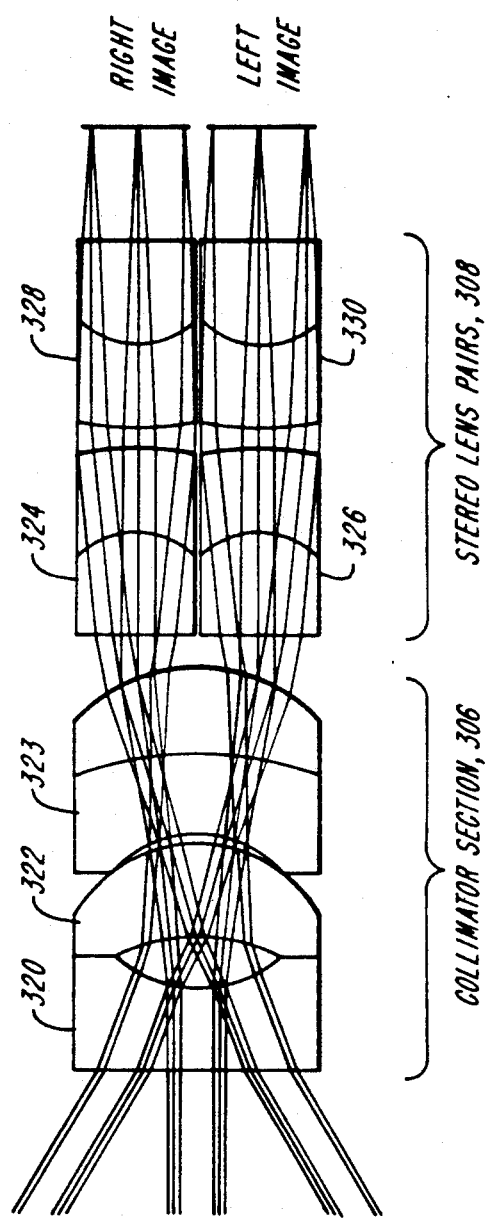

FIGS. 6 and 7 illustrate objective lens systems in which the collimator lens system is formed of a combination of singlet and doublet lenses. The embodiment of the objective system 100 illustrated in FIG. 6 includes in the collimator lens system 306 a singlet lens 310 coupled to a doublet lens 312, coupled to another singlet lens 313. The stereo lens pair system 308 is formed as in FIG. 2 by a pair of doublet lenses 314 ad 316 coupled to a second pair of doublet lenses 316 and 320. The full diameter lens system collimates object points. The critical requirement is that the collimator system present equal angle pairs from symmetrically disposed object points to the small stereo lens pairs. This can be accomplished with a doublet lens system as illustrated in FIG. 2, a GRIN lens system as illustrated in FIG. 5, combinations of singlets and doublets as illustrated in FIGS. 6 or 7, triplet lenses or combinations of the above. Of course, the stereo lens system can be formed of GRIN lenses also, as well as combinations of singlets, doublets, and triplets as above.

A working example of a set of lenses for implementation of the objective lens system 100 illustrated in FIG. 6 is set forth in Table B. As in Table A, the numerical value in the radius and thickness columns are in millimeters. The "GLASS" descriptions are standard optical glass characterizations as found in the product catalog of the Schott Glass Company of the Federal Republic of Germany. The "THICKNESS" column refers to the distance to the next optical surface. For example, in connection with surface 3, the number 1.5000 signifies 1.5 millimeters to surface 4. The column "RADIUS" refers to the radii of curvature of the respective curved surfaces.

In Table B lens surfaces 1, 2, 9, 16 and 17 do not correspond to actual lens surfaces.

TABLE B

STEREO OBJECTIVE, TYPE 3

| SRF | RADIUS | THICKNESS | APERTURE | GLASS | SPE |
|---|---|---|---|---|---|
| 1 | — | −3.222728 | 0.180000A | AIR | |
| 2 | — | 2.000000 | 3.000000 | SIO2 | C |
| 3 | 3.000000 | 1.130000 | 2.000000 | AIR | |
| 4 | −6.917339 | 1.500000 | 2.000000 | SF1 | |
| 5 | 9.000000 | 2.200000 | 3.000000 | LAKN12 | |
| 6 | −8.000000 | 0.505000 | 3.000000 | AIR | |
| 7 | −3.200000 | 2.500000 | 2.100000 | F4 | |
| 8 | −3.422239 | −1.400000 | 3.000000 | AIR | |
| 9 | — | 2.200000 | 1.000000 | AIR | |
| 10 | 44.701000 | 2.500000 | 1.500000 | LAK8 | |
| 11 | −2.100000 | 2.000000 | 1.500000 | SF1 | |
| 12 | −8.920000 | 0.500000 | 1.500000 | AIR | |
| 13 | 8.920000 | 2.000000 | 1.500000 | SF1 | |
| 14 | 2.100000 | 2.500000 | 1.500000 | LAK8 | |
| 15 | −44.701000 | 2.395144 | 1.500000 | AIR | |
| 16 | — | 0.001000 | 1.250000 | BK7 | |
| 17 | — | — | 1.250000 | AIR | |

FIG. 7 illustrates another collimator lens combination 306, employing a sequence of two singlet lenses 320 and 322 followed by doublet lenses 323. The physical characteristics for this sequence are set forth in Table C.

Table C is a working example of the objective lens system illustrated in FIG. 7.

In Table C lens surfaces 1, 2, 9, 16 and 17 do not correspond to physical lens surfaces.

TABLE C

STEREO VIDEO SYSTEM

| SRF | RADIUS | THICKNESS | APERTURE | GLASS | SPE |
|---|---|---|---|---|---|
| 1 | — | −3.095070 | 0.160000A | AIR | |
| 2 | — | 2.000000 | 3.000000 | SIO2 | C |
| 3 | 3.000000 | 1.245000 | 2.000000 | AIR | |
| 4 | −4.400000 | 2.200000 | 2.000000 | F4 | |
| 5 | −3.522702 | 0.244000 | 3.000000 | AIR | |
| 6 | −2.856443 | 2.000000 | 2.100000 | LAKN12 | |
| 7 | −9.000000 | 2.000000 | 3.000000 | SF1 | |
| 8 | −4.387343 | −1.400000 | 3.000000 | AIR | |
| 9 | — | 2.200000 | 1.000000 | AIR | |
| 10 | 44.701000 | 2.500000 | 1.500000 | LAK8 | |
| 11 | −2.100000 | 2.000000 | 1.500000 | SF1 | |
| 12 | −8.920000 | 0.500000 | 1.500000 | AIR | |
| 13 | 8.920000 | 2.000000 | 1.500000 | SF1 | |
| 14 | 2.100000 | 2.500000 | 1.500000 | LAK8 | |
| 15 | −44.701000 | 2.669074 | 1.500000 | AIR | |
| 16 | — | 0.001000 | 1.250000 | BK7 | |
| 17 | — | — | 1.250000 | AIR | |

As indicated in FIG. 1, the endoscope objective system 100 can be utilized in connection with optical fiber elements or a set of relay lenses 150 to conduct light from the objective system to the sensing element 152, 154. An example of the relay lens system 150 that can be employed with the objective system 100 is depicted in FIG. 3.

The relay lens system of FIG. 3 includes a plurality of rod relays 160, 162, 164 utilized in combination with objective system 100. Those skilled in the art will recognize that a wide range of relay lens systems can be employed with an objective system constructed in accordance with the invention.

Alternatively, an endoscope constructed in accordance with the invention can employ a conventional CCD array mounted within the same housing as the objective system. As indicated in FIG. 2, the CCD array can include left and right sensing elements 152, 154, disposed to receive the optical images generated at the output of doublets 118 and 120. The design and construction of CCD elements having more than one photosensitive region in a monolithic package is well known in the art. The electrical signals generated by the CCD array can be conducted from the housing by a conventional conduit. This configuration eliminates the requirement for a relay lens system or optical fibers.

The system 100 depicted in FIGS. 2 and 3 offers advantages for use in medical endoscopes and industrial borescopes. The configuration offers the advantage of being adaptable to fit into a small tube diameter, as small as 3 millimeters. The design also affords high resolution and low distortion for diagnostic and surgical use, and for high-accuracy industrial measurement applications.

It will thus be seen that the invention efficiently attains the objects set forth above, among those made apparent from the preceding description.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. A stereoscopic objective lens system for a stereo video endoscope, the objective lens system converting optical images of an object generated at an objective end of the objective system to pixel-mapped left and right optical images at an image plane end of the objective system, the objective lens system comprising, A. a gradient index collimator lens element proximate the objective end for collecting light from points on the object, said gradient index lens having a first optical axis, a selected diameter and a selected optical power, wherein said gradient index lens images the object points substantially to infinity so that light transmitted by the gradient index lens from the object points is substantially collimated, B. a right/left pair of stereo gradient index lenses situated adjacent said gradient index collimator lens for collecting light from said gradient index collimator lens, said first right/left pair of stereo gradient index lenses including, a right gradient lens and
a left gradient lens, the optical axis of said right stereo lens and the optical axis of said left stereo lens being substantially parallel to the optical axis of collimator lens, wherein said collimator lens and said right/left pair of stereo lenses cooperate so that the collimator lens presents equal-angle light ray pairs from symmetrically disposed object points to the right/left pair of stereo lenses, and said right stereo lens collects light from said collimator lens to generate a right image at the image plane, said left stereo lens collects light from said collimator lens to generate a left image at the image plane, such that corresponding portions of each left/right image are mapped to within a selected distance of each other.

2. A lens system according to claim 1, wherein said right stereo lens and said left stereo lens, are substantially identical.

3. A lens system according to claim 1 wherein the diameter of said right stereo lens and said left stereo lens, are approximately one-half the diameter of said collimator lens.

4. Stereoscopic endoscope apparatus for displaying stereoscopic images of an object, the apparatus comprising A. a stereoscopic objective lens system,
the objective lens system converting optical images of the object generated at an objective end of the objective system to pixel-mapped left and right optical images at an image plane end of the objective system, the objective lens system including,
(i) a collimator lens system proximate the objective end for collecting light from points on the object, said collimator lens system having a defined optical axis, a selected diameter and a selected optical power, such that said collimator lens system images the object points substantially to infinity so that light transmitted by said collimator lens system from the object points is substantially collimated, (ii) a right/left pair of stereo lens systems situated adjacent said collimator lens system for collecting light from said collimator lens system, said right/left pair of stereo lens systems including, a right stereo lens system having a defined optical axis and a selected diameter, a left stereo lens system having a defined optical axis and a selected diameter equal to the diameter of said right stereo lens system, the optical axis of said right lens system and the optical axis of said left lens system being substantially parallel to the defined optical axis of said collimator lens system, wherein said collimator lens system and said right/left pair of stereo lens systems cooperate so that the collimator lens system presents equal-angle light ray pairs from symmetrically disposed object points to said right/left pair of stereo lens systems.

5. An apparatus in accordance with claim 4 wherein at least one of said collimator lens systems or said right/left pair of stereo lens systems are formed of gradient index lenses and corresponding portions of each left/right image are mapped to within a selected distance of each other, and wherein at least one of said collimator lens systems or said right/left pair of stereo lens systems are formed of gradient index lenses.

6. An apparatus in accordance with either of claims 4 or 5 wherein the diameter of each of said left and right stereo lens systems is substantially one half the diameter of said collimator lens system.

7. An apparatus in accordance with claim 4 and further including right and left optical sensing means, situated at right and left regions of the image plane, respectively, for converting said right and left optical images to electrical signals representative of right and left video signals in response to said right and left optical images, respectively.

8. An apparatus in accordance with claim 5 and further including right and left optical sensing means, situated at right and left regions of the image plane, respectively, for converting said right and left optical images to electrical signals representative of right and left video signals in response to said right and left optical images, respectively.

9. Apparatus in accordance with either of claims 4 or 5 having aperture stops between said collimator and said right/left pair of stereo lens systems.

10. Apparatus according to either of claims 7 or 8, further comprising video monitor means, in electrical communication with said first and second optical sensing means, for displaying right and left video images in response to said electrical signals generated by the first and second optical sensing means.

11. Apparatus according to claim 7 wherein said right and left optical sensing means include at least one CCD element.

12. Apparatus according to claim 8 wherein said right and left optical sensing means include at least one CCD element.

13. Apparatus according to claim 11 wherein said objective lens system is contained within a housing, and said at least one CCD element is disposed within said housing in proximity to said objective lens system so that optical images generated by said objective lens system are transmitted to said at least one CCD element.

14. A stereoscopic endoscope apparatus in accordance with claim 4 wherein said collimator lens system comprises A. a first collimator doublet lens element proximate the objective end for collecting light from points on the object, said first doublet lens having a first optical axis, a selected diameter and a selected optical power, B. A second collimator doublet lens for collecting light from said first collimator doublet lens, said second collimator doublet lens being situated adjacent said first collimator doublet lens, so that the optical axis of said second collimator doublet lens is substantially collinear with the optical axis of the first collimator double lens, said second collimator doublet lens having a selected diameter and a selected optical power, wherein said first and second collimator doublet lenses cooperate to image the object points substantially to infinity so that light transmitted by the second collimator doublet lens from the object points is substantially collimated.

15. A stereoscopic apparatus in accordance with claim 4, wherein said collimator lens system comprises a gradient index lens providing substantially the same optical output as a doublet lens in imaging the object points substantially to infinity.

16. A stereoscopic apparatus in accordance with claim 4 wherein said collimator lens system comprises,
a first collimator singlet lens proximate the objective end for collecting light from points on the object,
a first collimator doublet lens for collecting light from said first collimator singlet lens, and
a second collimator singlet lens proximate to said first collimator doublet lens for collecting light from said first collimator doublet lens,
said collimator singlet lenses and said collimator doublet lens all having colinear optical axes and wherein said first and second collimator singlet lenses and said first collimator doublet lens cooperate to image the object points substantially to infinity.

17. A stereoscopic apparatus in accordance with claim 4 wherein said collimator lens system comprises,
a first collimator singlet lens proximate the objective end for collecting light from points on the objective,
a second collimator singlet lens for collecting light from said first collimator singlet lens, and
a first collimator doublet lens proximate said second collimator singlet lens for collecting light from said second collimator singlet lens, wherein said first and second collimator singlet lenses and said first collimator doublet lens cooperate to image the object points substantially to infinity.

* * * * *